United States Patent [19]
Manogue et al.

[11] Patent Number: 6,018,083
[45] Date of Patent: Jan. 25, 2000

[54] PROCESS FOR THE PRODUCTION OF FLUOROCARBONS

[75] Inventors: William H. Manogue; Mario Joseph Nappa, both of Newark, Del.; Allen Capron Sievert, Elkton, Mass.; V. N. Mallikarjuna Rao, Newark, Del.

[73] Assignee: E. I. du Pont de Nemours and Company, Wilmington, Del.

[21] Appl. No.: 09/283,450

[22] Filed: Apr. 1, 1999

Related U.S. Application Data

[60] Provisional application No. 60/080,708, Apr. 3, 1998.

[51] Int. Cl.[7] .............................. C07C 17/25; C07C 17/08
[52] U.S. Cl. .......................... 570/156; 570/157; 570/158; 570/168; 570/169
[58] Field of Search ..................................... 570/156, 157, 570/158, 168, 169

[56] References Cited

U.S. PATENT DOCUMENTS

| | | |
|---|---|---|
| 3,865,885 | 2/1975 | Bruce, Jr. . |
| 4,158,023 | 6/1979 | Von Halasz . |
| 4,978,649 | 12/1990 | Surovikin et al. . |
| 5,036,036 | 7/1991 | Lerou . |
| 5,043,491 | 8/1991 | Webster et al. . |
| 5,057,634 | 10/1991 | Webster et al. . |
| 5,068,472 | 11/1991 | Webster et al. . |
| 5,068,473 | 11/1991 | Kellner et al. . |
| 5,146,018 | 9/1992 | Kellner et al. . |

FOREIGN PATENT DOCUMENTS

| | | |
|---|---|---|
| 0 002 098 | 5/1979 | European Pat. Off. . |
| 902590 | 8/1962 | United Kingdom . |

*Primary Examiner*—Alan Siegel

[57] ABSTRACT

A process is disclosed for the separation of a mixture of HF and $CF_3CClFCF_3$. The process involves placing the mixture in a separation zone at a temperature of from about −30° C. to about 100° C. and at a pressure sufficient to maintain the mixture in the liquid phase, whereby an organic-enriched phase comprising less than 50 mole percent HF is formed as the bottom layer and an HF-enriched phase comprising more than 90 mole percent HF is formed as the top layer. The organic-enriched phase can be withdrawn from the bottom of the separation zone and subjected to distillation in a distillation column to recover essentially pure $CF_3CClFCF_3$. The distillate comprising HF and $CF_3CClFCF_3$ can be removed from the top of the distillation column while essentially pure $CF_3CClFCF_3$ can be recovered from the bottom of the distillation column. The HF-enriched phase can be withdrawn from the top of the separation zone and subjected to distillation in a distillation column. The distillate comprising HF and $CF_3CClFCF_3$ can be removed from the top of the distillation column while essentially pure HF can be recovered from the bottom of the distillation column. If desired, the two distillates can be recycled to the separation zone.

Also disclosed are compositions of hydrogen fluoride in combination with an effective amount of $CF_3CClFCF_3$ to form an azeotrope or azeotrope-like composition with hydrogen fluoride. Included are compositions containing from about 38.4 to 47.9 mole percent $CF_3CClFCF_3$.

Also disclosed are processes for producing 1,1,1,2,3,3,3-heptafluoropropane. One process uses a mixture comprising HF and $CF_3CClFCF_3$ and is characterized by preparing essentially pure $CF_3CClFCF_3$ as indicated above, and reacting the $CF_3CClFCF_3$ with hydrogen. Another process uses an azeotropic composition as described above, and reacts the $CF_3CClFCF_3$ with hydrogen in the presence of HF.

Also disclosed is a process for producing hexafluoropropene. This process is characterized by preparing essentially pure $CF_3CClFCF_3$ as indicated above, and dehalogenating the $CF_3CClFCF_3$.

3 Claims, 1 Drawing Sheet

PROCESS FOR THE PRODUCTION OF FLUOROCARBONS

This application claims the priority benefit of U.S. provisional application Ser. No. 60/080,708, filed Apr. 3, 1998.

FIELD OF THE INVENTION

The present invention relates to the synthesis of hexafluoropropylene and 1,1,1,2,3,3,3-heptafluoropropane.

BACKGROUND

Commercial methods for the preparation of hexafluoropropylene ($CF_3CF=CF_2$ or HFP), a fluoromonomer, typically involve temperatures greater than 600° C. The high reaction temperatures lead to the formation of perfluoroisobutylene, an extremely toxic compound which is costly to remove and destroy (e.g., see European Patent Application No. 002,098). Processes for the manufacture of HFP at lower temperatures based on the use of acyclic three-carbon hydrocarbons or partially halogenated three-carbon hydrocarbons are disclosed in U.S. Pat. Nos. 5,043,491, 5,057,634 and 5,068,472.

1,1,1,2,3,3,3-Heptafluoropropane ($CF_3CHFCF_3$ or HFC-227ea), a fire extinguishant, can be prepared by the reaction of HF with HFP in contact with activated carbon (e.g., see British Patent Specification No. GB 902,590). The manufacture of HFC-227ea in this instance is tied to the availability HFP.

There is a need for alternative methods of manufacturing HFP and HFC-227ea.

SUMMARY OF THE INVENTION

A process is provided for the manufacture of hexafluoropropylene and 1,1,1,2,3,3,3-heptafluoropropane. The process comprises (a) feeding 1,1,2-trichloro-3,3,3-trifluoropropene-1 ($CCl_2=CClCF_3$), HF and $Cl_2$ to a first reaction zone containing a catalyst comprising trivalent chromium and operating at a temperature of at least 250° C., but not more than about 325° C., to produce a reactor effluent comprising $C_3Cl_3F_5$, $C_3Cl_2F_6$, $CF_3CClFCF_3$, HCl and HF; (b) distilling the reactor effluent of (a) to produce (i) a low boiling stream comprising HCl, (ii) a reactant stream comprising an azeotrope of 2-chloro-1,1,1,2,3,3,3-heptafluoropropane HF and (iii) a high-boiling stream comprising $C_3Cl_2F_6$ and $C_3Cl_3F_5$; (c) reacting the 2-chloro-1,1,1,2,3,3,3-heptafluoropropane of reactant stream (ii) with hydrogen in the presence of a catalyst to produce a mixture comprising hexafluoropropylene and 1,1,1,2,3,3,3-heptafluoropropane; (d) feeding the $C_3Cl_2F_6$ and $C_3Cl_3F_5$ of high boiling stream (iii) along with HF to a second reaction zone containing a catalyst comprising trivalent chromium and operating at a temperature of at least about 375° C. to produce a reaction product comprising $CF_3CClFCF_3$ and HF; and (e) recycling the reaction product of (d) to the first reaction zone.

DETAILED DESCRIPTION

Figure 1:
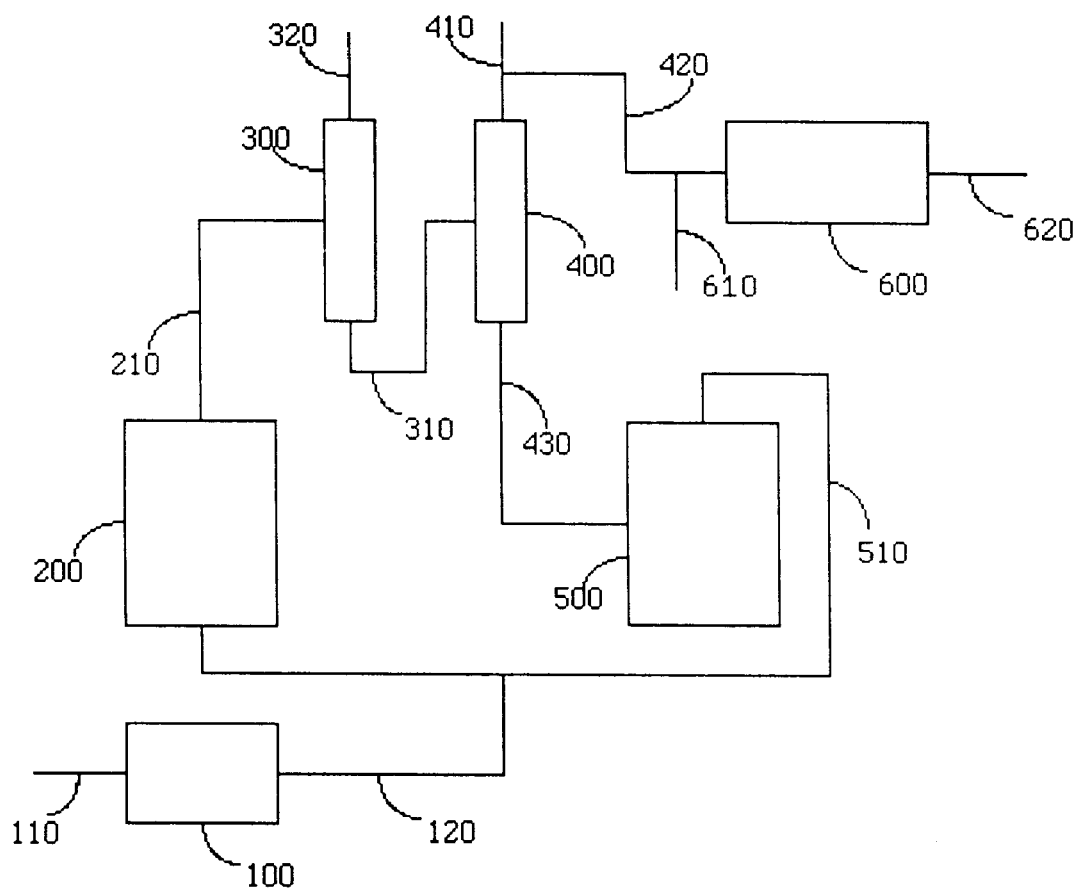
FIG. 1 is a schematic flow diagram of an embodiment of the process of this invention.

The present invention involves the use of $CCl_2=CClCF_3$ and $CF_3CClFCF_3$ in combination as materials for producing $CF_2=CFCF_3$ and $CF_3CHFCF_3$. The process of the invention uses an azeotropic composition of $CF_3CClFCF_3$ and HF as a precursor to the desired products. Further information on such azeotropes is provided in U.S. patent application Ser. No. 09/283,449, which is hereby incorporated by reference herein.

$Cl_2=CCl_2CF_3$, a feed material for step (a) above, may be derived, for example, by the chlorofluorination of hexachloropropylene. At least a portion of the $CF_3CClFCF_3$ is derived in accordance with step (d) above.

FIG. 1 is illustrative of one method of practicing this invention. Referring to FIG. 1, a feed mixture comprising hexachloropropylene (i.e., $CCl_2=CClCCl_3$ or HCP), chlorine and hydrogen fluoride and where the HF:HCP molar ratio is about 3:1, or more (the $Cl_2$:HCP ratio is typically about 1:1, or more), is passed through line (110) into reactor (100). Liquid phase, vapor phase or trickle bed reactors can be used. For the liquid phase and trickle bed reactors the reaction temperature is at least about 25° C. The trickle bed reactors are usually packed, e.g., with carbon, or can contain bubble trays; both modes are well known in engineering practice. For the vapor phase reactors, which can be either empty or packed (e.g., with carbon), the minimum reaction temperature is at least 150° C. The $CCl_2=CClCF_3$ starting material of step (a) can also be obtained by the chlorofluorination reaction of 2-fluoropropane over a divalent cobalt on an activated carbon catalyst as described in U.S. Pat. No. 3,865,885.

The reactor effluent from chlorofluorination reactor (100) comprising 1,1,2-trichloro-3,3,3-trifluoropropene-1 (i.e., $CCl_2=CClCF_3$ or FC-1213xa), chlorine, HF and HCl is passed through line (120) into line (510) where it is combined with the reaction effluent from reactor (500). The reactor (500) effluent comprises 2-chloro-1,1,1,2,3,3,3-heptafluoropropane (i.e., $CF_3CClFCF_3$ or CFC-217ba), HCl and HF.

The combined (100) and (500) reactor effluents are sent to reactor (200) which is maintained at a temperature within the range of about 250° C. to about 325° C. Reactor (200) is packed with a catalyst comprising trivalent chromium. Additional HF may be added, if required. A preferred catalyst is $Cr_2O_3$ prepared by the pyrolysis of $(NH_4)_2Cr_2O_7$ as described in U.S. Pat. No. 5,036,036.

The reactor (200) effluent comprising HF, $C_3Cl_3F_5$, $C_3Cl_2F_6$ and $C_3ClF_7$ is sent through line (210) into distillation column (300). The $C_3Cl_3F_5$ component is mainly composed of $CClF_2CCl_2CF_3$, $CCl_2FCClFCF_3$ and a small amount of $CClFCF_2CClF_2$. The $C_3Cl_2F_6$ component is mainly composed of $CF_3CCl_2CF_3$ and $CClF_2CClFCF_3$ and small amounts of $CClF_2CF_2CClF_2$. The $C_3ClF_7$ component is mainly composed of $CF_3CClFCF_3$. HCl and other low boiling components are removed through line (320) and the remainder of the reactor (200) effluent is sent through line (310) into a second distillation column (400). The bottom fraction from column (400) which comprises HF, $C_3Cl_3F_5$ and $C_3Cl_2F_6$ is sent through line (430) into reactor (500) which is maintained at a temperature of at least about 375° C. The reactor is packed with a catalyst comprising trivalent chromium. A preferred catalyst is the above-described $Cr_2O_3$ prepared by pyrolysis of $(NH_4)_2Cr_2O_7$. The effluent from reactor (500) comprising HCl, HF and CFC-217ba is removed through line (510) and sent to reactor (200).

HF/CFC-217ba azeotrope is removed from the top of column (400) through line (410). HF/CFC-217ba azeotrope is passed through line (420) into catalytic reactor (600) along with hydrogen which is fed through line (610). The reactor (600) product is removed through line (620) and comprises, HCl, HF, hexafluoropropylene (i.e., $CF_3CF=CF_2$ or HFP) and 1,1,1,2,3,3,3-heptafluoropropane ($CF_3CHFCF_3$ or HFC-227ea). The hydrogenolysis of step (c) may be conducted in the presence of HF. HFP and HFC-227ea can be isolated by conventional means. A portion of the azeotrope can be taken off through line (410) for other uses (e.g., the manufacture of $CF_3CF_2CF_3$).

The fluorination catalyst employed in steps (a) and (d) of the process of the invention may be supported or unsupported. Any of the fluorination catalysts described in the prior art may be used such as oxides, halides and oxyhalides of aluminum, cobalt, manganese, iron and particularly chromium. Suitable chromium-containing catalysts include oxide, hydroxide, oxyhalide, halides, inorganic acid salts, basic chromium fluorides and especially preferred are the chromium oxide catalysts described in U.S. Pat. No. 5,036,036. The catalysts may be given a prefluorination treatment by passing hydrogen fluoride, with or without an inert diluent such as nitrogen, over the catalyst at a temperature within the range of about 250 to 450° C. prior to use.

The operating pressure of the process of the invention is dependent on the product isolation scheme employed and is generally within the range of from about 101 kPa to about 5000 kPa.

The reaction zone of steps (a) and (d) may consist of one or two reactors.

CFC-217 ba may be reacted with hydrogen to form a product comprising HFP and HFC-227ea by contacting the CFC-217ba with hydrogen at an elevated temperature in the vapor phase over a catalyst comprising at least one component selected from the group consisting of elemental metals, metal oxides, metal halides and metal oxyhalides; wherein the metal of said hydrodehalogenation catalyst component is selected from copper, nickel, chromium and mixtures thereof and the halogen of said halides and said oxyhalides is selected from fluorine, chlorine and mixtures thereof. Greater details of the reaction with hydrogen are described in U.S. Pat. No. 5,057,634 which is incorporated herein by reference. Another useful catalyst comprises a three-dimensional matrix carbonaceous material such as that described in U.S. Pat. No. 4,978,649.

Alternatively, CFC-217ba can be converted to a product comprising HFC-227ea and HFP by contacting CFC-217ba with hydrogen at an elevated temperature in the vapor phase over a catalyst comprising at least one metal selected from the group consisting of rhenium, ruthenium, rhodium and palladium. The reaction temperature for these metal-containing catalysts is at least about 100° C. The reaction temperature when other catalysts are used is normally at least about 300° C. In any case, the reaction temperature is normally less than 500° C.

The reaction pressure is normally within the range of about 100 kPa to about 7000 kPa. Typically, the mole ratio of hydrogen to CFC-217ba is from 0.5:1 to 25:1, preferably from 1:1 to 5:1.

Those skilled in the art will recognize that since the drawings are representational, it will be necessary to include further items of equipment in an actual commercial plant, such as pressure and temperature sensors, pressure relief and control valves, compressors, pumps, storage tanks and the like. The provision of such ancillary items of equipment would be in accordance with conventional chemical engineering practice.

The reaction zone and its associated feed lines, effluent lines and associated units should be constructed of materials resistant to hydrogen fluoride and hydrogen chloride. Typical materials of construction, well-known to the fluorination art, include stainless steels, in particular of the austenitic type, the well-known high nickel alloys, such as Monel® nickel-copper alloys, Hastelloy® nickel-based alloys and, Inconel® nickel-chromium alloys, and copper-clad steel.

Without further elaboration, it is believed that one skilled in the art can, using the description herein, utilize the present invention to its fullest extent. The following specific embodiments are, therefore, to be construed as merely illustrative, and do not constrain the remainder of the disclosure in any way whatsoever.

EXAMPLES

LEGEND

| | |
|---|---|
| 13 is $CClF_3$ | 23 is $CHF_3$ |
| 112 is $CCl_2FCCl_2F$ | 113 is $CCl_2FCClF_2$ |
| 114 is $CClF_2CClF_2$ | 115 is $CClF_2CF_3$ |
| 125 is $CHF_2CF_3$ | 214ab is $CCl_2FCCl_2CF_3$ |
| 215aa is $CClF_2Cl_2CF_3$ | 215bb is $CCl_2FCClFCF_3$ |
| 215ca is $CCl_2FCF_2CClF_2$ | 216aa is $CF_3CCl_2CF_3$ |
| 216ba is $CClF_2CClFCF_3$ | 216ca is $CClF_2CF_2CClF_2$ |
| 217ba is $CF_3CClFCF_3$ | 217ca is $CClF_2CF_2CF_3$ |
| 218 is $CF_3CF_2CF_3$ | 226da is $CF_3CHClCF_3$ |
| 226ea is $CClF_2CHFCF_3$ | 227ea is $CF_3CHFCF_3$ |
| 236ea is $CHF_2CHFCF_3$ | 236fa is $CF_3CH_2CF_3$ |
| 1213xa is $CCl_2=CClCF_3$ | 1214 is $C_3Cl_2F_4$ |
| 1215 is $C_3ClF_5$ | 1215xc is $CF_2=CClCF_3$ |
| 1225zc is $CF_2=CHCF_3$ | HFP is $CF_3CF=CF_2$ |

CT is contact time
P is pressure
T is temperature

General Procedure for Product Analysis

The following general procedure is illustrative of the method used. Part of the total reactor effluent was sampled on-line for organic product analysis using a Hewlett Packard HP 5890 gas chromatograph equipped with a 20' (6.1 m) long×1/8" (0.32 cm) diameter tubing containing Krytox® perfluorinated polyether on an inert carbon support and within a flame ionization detector. The helium flow was 35 mL/min. Gas chromatographic conditions were 70° C. for an initial hold period of three minutes followed by temperature programming to 180° C. at a rate of 6° C./minute.

The bulk of the reactor effluent containing organic products and also inorganic acids such as HCl and HF was treated with aqueous caustic prior to disposal.

EXAMPLE 1

Chlorofluorination of FC-1213xa

Chromium oxide (47.25 g, 35 mL, 10–20 mesh, (2.0–0.84 mm)), obtained from the pyrolysis of ammonium dichromate prepared according to the procedure described in U.S. Pat. No. 5,036,036, was placed in a 5/8" (1.58 cm) diameter Inconel® nickel alloy reactor heated in a fluidized sand bath. It was heated to 175° C. in a flow of nitrogen (50 cc/min) at which time HF flow (50 cc/min) was also started through the reactor. After 15 minutes, the nitrogen flow was decreased to 20 cc/min and the HF flow increased to 80 cc/min. The reactor temperature was gradually increased to 400° C. during a 2 hour period and maintained at 400° C. for an additional 30 minutes. At the end of this period the reactor was brought to the desired operating temperature for catalyst evaluation under a nitrogen flow.

The results of the chlorofluorination reaction are shown in Table 1 in area %.

TABLE 1

| T °C. | Molar Ratio HF:1213xa:Cl$_2$ | C.T. Sec. | % 217ba | % 226da | % 216aa | % 216ba | % 215aa | % Others |
|---|---|---|---|---|---|---|---|---|
| 250 | 20:1:2 | 60 | 0.3 | 1.8 | 10.1 | 9.9 | 74.9 | 3.0 |
| 260 | 20:1:2 | 60 | 0.5 | 2.5 | 15.6 | 10.8 | 67.8 | 2.8 |
| 260 | 20:1:4 | 60 | 0.5 | 0.7 | 10.6 | 13.2 | 72.4 | 2.6 |
| 260 | 10:1:2 | 60 | 0.2 | 0.3 | 5.7 | 9.7 | 82.4 | 1.7 |
| 260 | 20:1:4 | 30 | 0.5 | 0.8 | 8.5 | 11.8 | 76.2 | 2.3 |
| 275 | 20:1:2 | 30 | 1.1 | 2.5 | 23.4 | 12.4 | 57.8 | 2.8 |
| 275 | 20:1:2 | 60 | 1.0 | 2.8 | 27.8 | 11.2 | 54.9 | 2.4 |
| 275 | 20:1:4 | 15 | 1.5 | 1.1 | 16.0 | 14.9 | 64.4 | 2.1 |
| 300 | 10:1:2 | 30 | 1.3 | 1.1 | 45.7 | 9.5 | 40.9 | 1.5 |
| 300 | 20:1:2 | 30 | 3.1 | 1.9 | 48.3 | 12.8 | 31.6 | 2.2 |
| 300 | 20:1:2 | 15 | 3.4 | 2.7 | 45.4 | 11.4 | 34.6 | 2.5 |
| 325 | 6:1:2 | 30 | 3.9 | 0.0 | 80.7 | 9.7 | 4.7 | 1.0 |

Others include mostly 1215, as well as 113, 114, 115, 1214, 215ca, 216ca and 217ca.

EXAMPLE 2

Chlorofluorination of FC-1213xa

The reactor used in Example 1 was charged with a 20% CrCl$_3$/carbon catalyst (6.15 g, 15 mL, 10–20 mesh, (2.0–0.84 mm)), prepared as described in Example 1 of U.S. Pat. No. 3,632,834, and activated as described above in Example 1.

The contact time for each run was 15 seconds. The results of the chlorofluorination reaction are shown in Table 2 in area %.

TABLE 2

| T °C. | Molar Ratio HF:1213xa:Cl$_2$ | % 216aa | % 216ba | % 1214 | % 215aa | % 215bb | % 1213xa | % 214ab | % Others |
|---|---|---|---|---|---|---|---|---|---|
| 300 | 20:1:4 | 4.0 | 0.2 | 6.5 | 19.5 | 6.9 | 61.3 | 0.0 | 1.9 |
| 325 | 20:1:4 | 8.7 | 0.5 | 3.7 | 39.1 | 7.1 | 39.7 | 0.0 | 1.3 |
| 325 | 20:1:2 | 14.6 | 0.4 | 3.7 | 36.1 | 6.6 | 37.2 | 0.0 | 1.4 |
| 350 | 20:1:4 | 16.1 | 1.0 | 3.1 | 50.7 | 7.9 | 0.0 | 19.1 | 1.9 |
| 350 | 6:1:1 | 13.6 | 0.5 | 2.5 | 51.9 | 4.3 | 1.2 | 25.0 | 1.2 |

Others include mostly 1215, as well as 13, 112, 113, 216ca, 226da and 217ba.

EXAMPLE 3

Fluorination of FC-216aa

The reactor and catalyst treatment were the same as those described in Example 1. A fresh sample of chromium oxide catalyst was used.

The contact time for each run was 30 seconds. The results of the fluorination reaction are shown in Table 3 in mol %.

TABLE 3

| T °C. | Molar Ratio HF:216aa | % 218 | % 217ba | % 1215 | % 226da | % 216aa | % Others |
|---|---|---|---|---|---|---|---|
| 375 | 4:1 | 0.2 | 7.4 | 0.6 | 0.7 | 90.2 | 0.8 |
| 400 | 4:1 | 0.6 | 18.2 | 0.7 | 0.9 | 78.7 | 0.9 |
| 400 | 8:1 | 0.6 | 22.2 | 1.0 | 0.9 | 74.5 | 0.8 |
| 400 | 12:1 | 0.6 | 23.8 | 1.3 | 0.9 | 72.4 | 0.9 |
| 400 | 20:1 | 0.6 | 28.2 | 1.8 | 1.7 | 66.5 | 1.2 |
| 425 | 20:1 | 1.3 | 53.7 | 1.6 | 1.7 | 39.7 | 1.9 |

Others include mostly 23, 115, 125, 1214, 1215, 227ea, 216ba and 217ca.

EXAMPLE 4

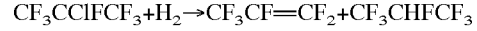

$CF_3CClFCF_3 + H_2 \rightarrow CF_3CF=CF_2 + CF_3CHFCF_3$

A 15" (38.1 cm)×3/8" (0.95 cm) O.D. Inconel™ 600 nickel alloy U-tube reactor was charged with 5% Re/Acid-Washed Carbon (2.4 g, 6.25 mL). The H$_2$:CFC-217ba molar ratio was 2:1. Results (in mol %) at various conditions are in Table 4.

TABLE 4

| T °C. | P psig (kPa) | CT min. | % Conv. 217ba | % Sel. HFP | % Sel. 1225zc | % Sel. 227ea | % Sel. 226ea | % Sel. Other |
|---|---|---|---|---|---|---|---|---|
| 260 | 0 (101) | 1.1 | 100 | 23 | 0.6 | 71 | 3.7 | 1.3 |
| 260 | 38 (363) | 1.3 | 98 | 18 | 0.6 | 73 | 6.6 | 1.3 |
| 260 | 100 (791) | 1.1 | 80 | 16 | 0.5 | 76 | 6.2 | 1.3 |
| 280 | 0 (101) | 1.0 | 100 | 25 | 1.7 | 68 | 2.6 | 2.3 |
| 280 | 30 (308) | 1.0 | 100 | 18 | 1.8 | 71 | 6.4 | 3.0 |
| 280 | 100 (791) | 2.1 | 100 | 7 | 2.8 | 69 | 16.4 | 4.5 |
| 300 | 0 (101) | 0.3 | 100 | 25 | 1.6 | 69 | 2.0 | 2.2 |
| 300 | 0 (101) | 0.5 | 100 | 26 | 2.4 | 67 | 1.7 | 2.9 |
| 300 | 0 (101) | 1.0 | 100 | 23 | 4.0 | 66 | 1.7 | 4.4 |

EXAMPLE 5

A 15" (38.1 cm)×1/4" (0.64 cm) O.D. Hastelloy™ C-276 nickel alloy U-tube reactor was charged with 1% Re/Acid-Washed Carbon calcined at 925° C. (2.59 g, 6.25 mL). The reaction pressure was 0 psig (101.3 kPa). Results (in mol %) at various conditions are shown in Table 5.

TABLE 5

| T °C. | Mol $H_2$:217ba | CT sec. | % Conv. 217ba | % Sel. HFP | % Sel. 227ea | % Sel. 236fa | % Sel. 226ea | % Sel. Other |
|---|---|---|---|---|---|---|---|---|
| 325 | 2 | 31 | 100 | 4 | 43 | 1.5 | 43.4 | 8.0 |
| 325 | 2 | 16 | 80 | 18 | 36 | 0.6 | 42.0 | 3.6 |
| 350 | 2 | 15 | 85 | 18 | 36 | 1.2 | 40.1 | 5.5 |
| 325 | 4 | 30 | 76 | 29 | 40 | 0.9 | 27.2 | 3.3 |
| 325 | 4 | 6 | 23 | 58 | 35 | 0.2 | 4.1 | 3.1 |
| 350 | 4 | 6 | 24 | 59 | 32 | 0.7 | 3.0 | 4.5 |
| 350 | 4 | 3 | 8 | 67 | 24 | 0.9 | 0.4 | 7.7 |
| 360 | 4 | 3 | 5 | 64 | 25 | 1.1 | 0.2 | 9.9 |

EXAMPLE 6

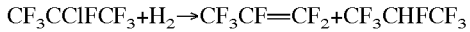

A 15" (38.1 cm)×3/8" (0.95 cm) O.D. Inconel™ 600 nickel alloy U-tube reactor was charged with 1% Ru/Acid-Washed Carbon (1.9 g, 6.25 mL. The reaction pressure was 0 psig (101.3 kPa). Results (in mol %) at various conditions are shown in Table 6.

TABLE 6

| T °C. | Mol $H_2$:217ba | CT min. | % Conv. 217ba | % Sel. HFP | % Sel. 227ea | % Sel. 226ea | % Sel. Other |
|---|---|---|---|---|---|---|---|
| 200 | 4 | 0.30 | 84 | 7 | 74 | 5 | 13 |
| 175 | 4 | 0.32 | 46 | 10 | 72 | 4 | 15 |
| 213 | 2 | 0.30 | 81 | 9 | 75 | 6 | 9 |
| 200 | 1 | 0.31 | 50 | 15 | 74 | 5 | 6 |

EXAMPLE 7

A 15" (38.1 cm)×1/4" (0.64 cm) O.D. Inconel™ 600 nickel alloy U-tube reactor was charged with carbon which was a three-dimensional matrix carbonaceous material (2.36 g, 6.25 mL, 20–30 mesh (0.84–0.59 mm)). The reaction pressure was 0 psig (101.3 kPa) for the first Table 7 entry and 30 psig (308 kPa) for all the others. The $H_2$:CFC-217ba molar ratio was 4:1 for the first entry and 16:1 for all the others. Results (in mol %) at various conditions are shown in Table 7.

TABLE 7

| T °C. | CT min. | % Conv. 217ba | % Sel. HFP | % Sel. 227ea | % Sel. 236ea | % Sel. 1215xc |
|---|---|---|---|---|---|---|
| 350 | 0.10 | 10 | 65 | 27 | 4 | 0.9 |
| 350 | 0.12 | 11 | 61 | 28 | 8 | 0.8 |
| 370 | 0.12 | 12 | 61 | 27 | 9 | 1.0 |
| 400 | 0.12 | 15 | 59 | 27 | 10 | 1.2 |
| 400 | 0.06 | 12 | 68 | 24 | 5 | 0.7 |
| 425 | 0.06 | 14 | 68 | 24 | 5 | 0.8 |

TABLE 7-continued

| T °C. | CT min. | % Conv. 217ba | % Sel. HFP | % Sel. 227ea | % Sel. 236ea | % Sel. 1215xc |
|---|---|---|---|---|---|---|
| 475 | 0.05 | 24 | 63 | 27 | 7 | 0.7 |
| 450 | 0.05 | 13 | 62 | 31 | 5 | 0.4 |
| 450 | 0.11 | 13 | 52 | 40 | 6 | 0.4 |

EXAMPLE 8

$CF_3CClFCF_3 + H_2 \rightarrow CF_3CF=CF_2 + CF_3CHFCF_3$

The same reactor and catalyst as used for Example 7 was used. The reaction pressure was 0 psig (101.3 kPa) and the $H_2$:CFC-217ba molar ratio was 4:1. Results (in mol %) at various conditions are shown in Table 8.

TABLE 8

| T °C. | CT min. | % Conv. 217ba | % Sel. HFP | % Sel. 227ea | % Sel. 236ea | % Sel. 1215xc | % Sel. Others |
|---|---|---|---|---|---|---|---|
| 325 | 0.10 | 14 | 43 | 20 | 2 | 0.7 | 1.6 |
| 350 | 0.10 | 11 | 62 | 28 | 4 | 1.2 | 2.6 |
| 350 | 0.05 | 9 | 65 | 27 | 5 | 0.9 | 3.0 |
| 350 | 0.50 | 9 | 56 | 32 | 6 | 2.4 | 4.4 |

What is claimed is:

1. A process for the manufacture of $CF_2=CFCF_3$ and $CF_3CHFCF_3$, comprising:

(a) feeding $CCl_2=CClCF_3$, HF and $Cl_2$ to a first reaction zone containing a catalyst comprising trivalent chromium and operating at a temperature of at least 250° C., but not more than about 325° C., to produce a reactor effluent comprising $C_3Cl_3F_5$, $C_3Cl_2F_6$, $CF_3CClFCF_3$, HCl and HF;

(b) distilling the reactor effluent of (a) to produce (i) a low boiling stream comprising HCl, (ii) a reactant stream comprising an azeotrope of $CF_3CClFCF_3$ and HF and (iii) a high-boiling stream comprising $C_3Cl_2F_6$ and $C_3Cl_3F_5$;

(c) reacting the $CF_3CClFCF_3$ of reactant stream (ii) with hydrogen in the presence of a catalyst to produce a mixture comprising $CF_2=CFCF_3$ and $CF_3CHFCF_3$;

(d) feeding the $C_3Cl_2F_6$ and $C_3Cl_3F_5$ of high boiling stream (iii) along with HF to a second reaction zone containing a catalyst comprising trivalent chromium and operating at a temperature of at least about 375° C. to produce a reaction product comprising $CF_3CClFCF_3$ and HF; and (e) recycling the reaction product of (d) to the first reaction zone.

2. The process of claim 1 wherein the $CCl_2=CClCF_3$ of (a) is derived by the chlorofluorination of $CCl_2=CClCCl_3$.

3. The process of claim 1 wherein the hydrogenolysis of (c) is conducted in the presence of HF.

* * * * *